US006221054B1

(12) United States Patent
Martin et al.

(10) Patent No.: US 6,221,054 B1
(45) Date of Patent: Apr. 24, 2001

(54) DEVICE FOR DISPENSING A FLUID PRODUCT CONTAINING TWO COMPONENTS

(75) Inventors: Claude-Georges Martin, Iville; Laurent Arghyris, Sotteville-les-Rouen, both of (FR)

(73) Assignee: Valois, S.A., Le Neuborg (FR)

( * ) Notice: Subject to any disclaimer, the term of this patent is extended or adjusted under 35 U.S.C. 154(b) by 0 days.

(21) Appl. No.: 09/319,226

(22) PCT Filed: Dec. 3, 1997

(86) PCT No.: PCT/FR97/02183

§ 371 Date: Sep. 13, 1999

§ 102(e) Date: Sep. 13, 1999

(87) PCT Pub. No.: WO98/24556

PCT Pub. Date: Jun. 11, 1998

(30) Foreign Application Priority Data

Dec. 6, 1996 (FR) .................................................. 96 14994

(51) Int. Cl.$^{7}$ .................................................... A61M 37/00

(52) U.S. Cl. .......................... 604/218; 604/181; 604/228; 604/403

(58) Field of Search ................................. 604/82, 89–91, 604/218, 228, 181, 187, 403, 416; 600/575, 576, 578, 579

(56) References Cited

U.S. PATENT DOCUMENTS 4,715,854 12/1987 Vaillancourt .
5,383,864 * 1/1995 Van Den Heuvel ................. 604/218
5,518,005 * 5/1996 Brannon .............................. 128/765
5,637,100 * 6/1997 Sudo ................................... 604/238
5,716,339 * 2/1998 Tanaka et al. ......................... 604/89
6,050,957 * 4/2000 Desch .................................. 600/579
6,059,755 * 5/2000 Michel ................................ 604/207

FOREIGN PATENT DOCUMENTS 94 03 512 6/1994 (DE) .

* cited by examiner

*Primary Examiner*—John G. Weiss
*Assistant Examiner*—David J. Cho
(74) *Attorney, Agent, or Firm*—Sughrue, Mion, Zinn, Macpeak & Seas, PLLC

(57) ABSTRACT

A device for dispensing fluid products having a dispensing member (1), such as a pump, mounted on a container (2), and an actuating member (3), such as a thruster, for dispensing the product. The device has two reservoirs of products (10, 20) arranged such that they are successively emptied, the product contained in the second reservoir (20) being dispensed only when the first reservoir (10) is empty, characterized in that the first reservoir (10) is fixed to the body of the dispensing member (1) or to a support piece (9) of the body, and extends to the bottom of the container at least partially inside the second reservoir (20).

6 Claims, 3 Drawing Sheets

DEVICE FOR DISPENSING A FLUID PRODUCT CONTAINING TWO COMPONENTS

BACKGROUND OF THE INVENTION

1. Field of the Invention

The present invention relates to a fluid product dispensing device consisting of two components, i.e. that enables two different products to be dispensed.

"Different" products can either refer to products with different compositions or different concentrations of the same product.

2. Related Art

There are many examples, particularly when treating certain illnesses, where the utilization of a single product is not sufficient or does not provide satisfactory results for the treatment concerned. In order to improve the treatment it is often necessary to combine two different products or two different concentrations of the same product, meaning that the user must have two product dispensers available. This has a number of drawbacks, for instance the utilization of several dispensers increases the cost of the treatment. Also, when two different products are utilized, one must generally be dispensed before the other. There is a risk of confusion or error concerning which dispenser is chosen by the user and which could result in a lack of efficiency in the treatment should the products be interchanged and/or should the order in which the two different products are dispensed become confused. Moreover, the utilization of two dispensers is not user friendly and requires extra space that can also be problematic.

SUMMARY OF THE INVENTION

The present invention aims to avoid the above-mentioned drawbacks.

In particular, the present invention aims to provide a single fluid product dispensing device that enables two different fluids to be dispensed from the same dispenser.

The present invention also aims to provide a fluid product dispenser of this kind that enables treatment to be achieved that is as efficient as possible at a cost that is as low as possible.

Another aim of the present invention is to provide a fluid product dispenser of this kind that avoids the risk of confusing two products to be dispensed, thus improving safety for the user.

Therefore, the present invention relates to a fluid product dispenser device that comprises a dispensing component such as a pump mounted on a recipient, and an actuating component such as a push button to dispense the product, the device comprising two product chambers fitted such that they are emptied successively, the product contained in the second chamber only being dispensed once the first chamber is empty, the first chamber being fastened to the body of the dispensing component or to a support part of said body and extending to the bottom of the recipient at least partly inside the second chamber.

Preferably, the first chamber is connected to the dispensing component and the second chamber is connected to said first chamber by a sealing part that prevents the product contained in the second chamber from flowing towards the dispensing component for as long as the first chamber still contains any product, and that releases said flow when said first chamber is empty such that when the device is subsequently actuated, the product that is contained in the second chamber is dispensed.

Advantageously, the first chamber is connected to the dispensing component on one side and comprises a connecting channel to the second chamber on the other side,. said first chamber comprising a follow-through piston that is displaced while remaining leaktight in said first chamber each time the device is actuated to compensate for the volume that is dispensed each time the device is actuated, the displacement of said follow-through piston simultaneously drawing in product from the second chamber in the upstream section of the first chamber located behind said follow-through piston in the direction of flow of the product, and when said follow-through piston has reached the end position in which the first chamber is empty, said follow-through piston operates in conjunction with means of passage to create a passage between said upstream section of the first chamber and the dispensing component, thus enabling the product drawn in said upstream section of the first chamber and/or the product remaining in the second chamber to be dispensed.

Advantageously, said means of passage are constituted by one or more grooves provided at the downstream end of the lateral surface of the first chamber.

The first chamber is fastened to the body of the dispensing component or to a support part of the body and extends to the bottom of the recipient at least partly inside the second chamber.

Advantageously, said first chamber is constructed as part of the body of the dispensing component or with the support part of said body.

BRIEF DESCRIPTION OF THE DRAWINGS

Other characteristics, aims and advantages of the present invention will be better understood from the following detailed description. The description is a non-limitative example and refers to the attached figures where.

DETAILED DESCRIPTION OF THE DRAWINGS

Figure 1:
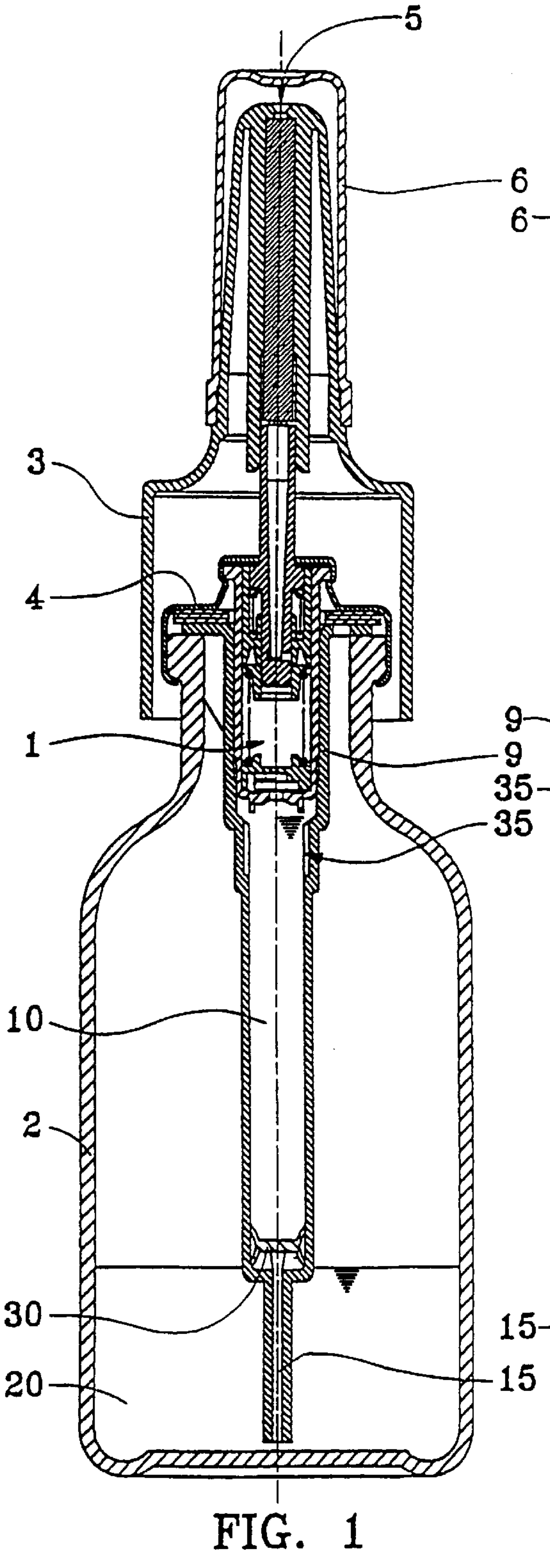
FIG. 1 is a schematic cross section of a device according to the invention before being utilized for the first time.

Referring to the figures, the dispenser comprises a dispensing component such as a pump 1 mounted on a recipient 2 using, for example, a fastening part such as a ring 4 that can be locked, crimped or fastened by any other means onto the collar of recipient 2. Said pump generally comprises a push-button 3 that is provided with a dispensing aperture 5 in order to dispense the product. Advantageously, the pump also comprises a spray nozzle 7 located near said dispensing aperture 5 to spray the product and a protective cap 6 can be provided to protect aperture 5 after the device has been used.

According to the invention, the device comprises two product chambers 10 and 20 in recipient 2, each chamber 10 and 20 comprising a different product either in terms of composition or concentration.

According to the invention, these two product chambers 10 and 20 are fitted such that they are successively emptied, i.e. the product contained in the second chamber 20 is only dispensed once the first chamber 10 is completely empty. In order for this to be achieved, one end of first chamber 10 is advantageously connected to pump 1, for example by an inlet valve, and said second chamber 20 is connected to the other end of first chamber 10. According to the invention, the connection between second chamber 20 and first chamber 10 is achieved by a sealing part 30 that prevents the product contained in second chamber 20 from flowing towards pump 1 such that when the device is actuated, the product dispensed is the product in chamber 10, the product contained in second chamber 20 being confined behind said sealing part 30. This sealing part 30 is intended to free the passage between the second chamber 20 and pump 1 when first chamber 10 is completely empty such that when the device is subsequently actuated, the product contained in second chamber 20 is dispensed.

Advantageously, this is achieved due to pump 1 not requiring another intake of air in order to operate and due to sealing part 30 acting as a follow-through piston in first chamber 10 such that each time the device is actuated a dose of product contained in first chamber 10 is dispensed and the volume of this dispensed dose is compensated by said follow-through piston 30 being displaced inside first chamber 10. As the second chamber 20 is connected to first chamber 10 on the other side of said follow-through piston 30 when said follow-through piston is displaced in first chamber 10, the product contained in second chamber 20 is drawn in upstream of said follow-through piston 30 in first chamber 10.

Figure 2:
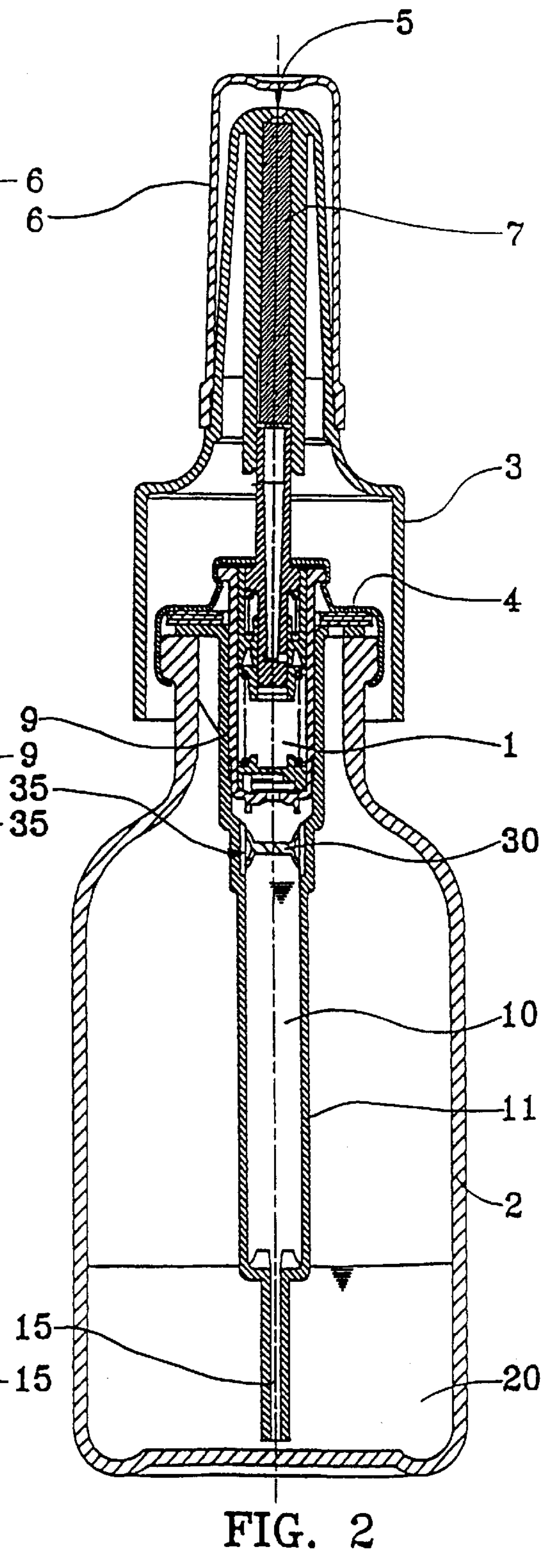
FIG. 2 shows a similar cross section to that in FIG. 1 after the device has been actuated once or several times.

When first chamber 10 is completely emptied, follow-through piston 30 reaches an end position in said first chamber 10 where means of passage 35 are provided to create a passage between the product contained upstream of said follow-through piston 30 and pump 1. Advantageously, these means of passage are constituted by one or more grooves provided in the lateral surface 11 of first chamber 10 at said end position of follow-through piston 30 which thereby constitutes said empty chamber. As seen in FIGS. 1 and 2, that show the two end positions of follow-through piston 30, when follow-through piston 30 reaches the end position that constitutes the empty first chamber 10, said first chamber 10 is in fact filled once again with product from second chamber 20. This is shown in FIG. 2 by a decrease in the level of product contained in second chamber 20. Therefore, "empty first chamber" means that the product contained in first chamber 10 has been completely dispensed and not that there is no more product contained in said first chamber.

Therefore, once the product contained in the first chamber has been completely dispensed, follow-through piston 30 reaches the end position where it operates in conjunction with passage means 35, that enable the product upstream of said follow-through piston 30 to be dispensed towards pump 1, such that when the device is subsequently actuated the product that was initially contained in second chamber 20 is dispensed.

Figure 3:
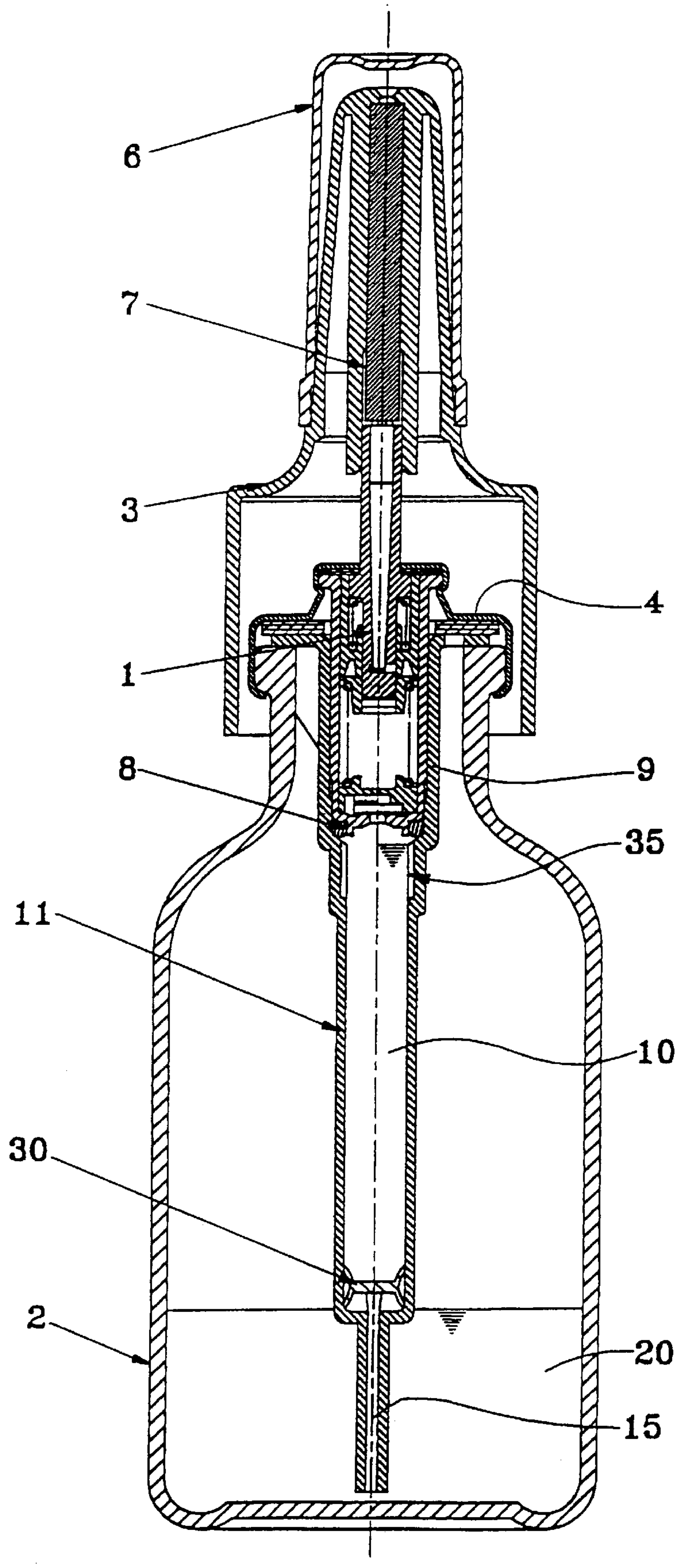
FIG. 3 shows a construction modification of the device in FIG. 1.

Preferably, first chamber 10 is directly connected to the dispensing component 1, i.e. the pump, on one side and comprises a connecting channel 15 on the other side that extends close to the bottom of recipient 2 where it is connected to second chamber 20 that is constituted directly by recipient 2. According to a first construction modification, first chamber 10 is constituted in a single part with the pump body and/or with a support part 9 of the pump body, as shown in FIGS. 1 to 3. The pump body is received inside this support part 9 that is positioned on the collar of the recipient, but it is also possible for this support part 9 to be eliminated and for the pump body to be positioned directly onto the collar of the recipient. In the example shown in FIGS. 1 and 2, leaktightness is achieved between the pump body and support part 9 by radial gripping whereas in the example shown in FIG. 3 leaktightness is achieved between support part 9 and the pump body by a seal that is advantageously toric 8.

Figure 4:
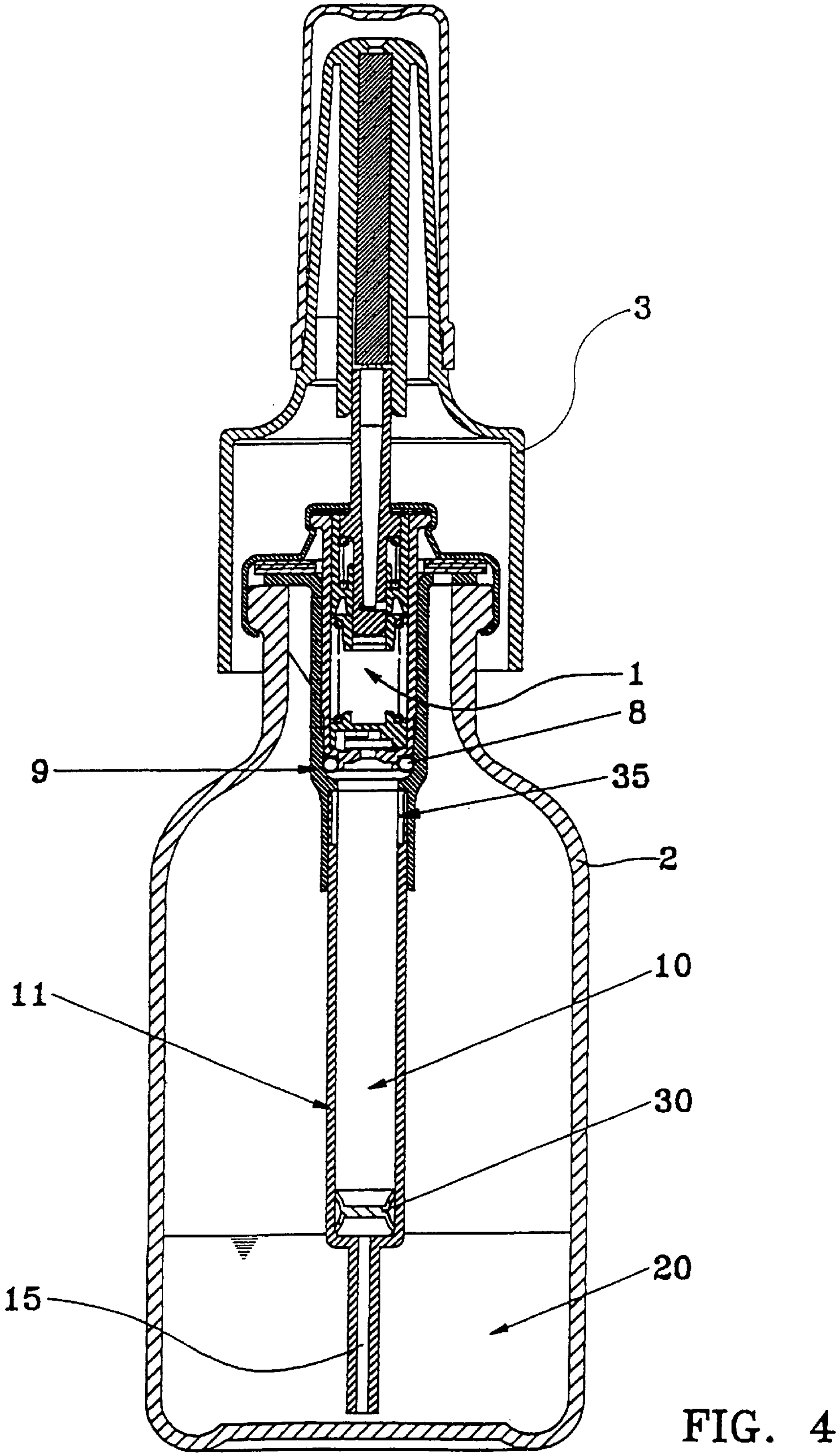
FIG. 4 is a similar cross section to that in FIG. 3 showing another construction modification of the device of the invention.

In the example shown in FIG. 4, first chamber 10 is fastened to support part 9, for example by lateral surface 11 radially gripping a lower end of said support part 9. In this example, leaktightness between the pump body and support part 9 is also achieved using a seal 8.

Therefore, during operation, when the user presses push-button 3 the first product to be dispensed is that contained in first chamber 10 until said first chamber is completely empty. The follow-through piston 30 then reaches the end position where it operates in conjunction with passage means 35 and the product that has been drawn in upstream of said follow-through piston 30 from second chamber 20 may be dispensed when the dispenser is subsequently actuated. From then onward, first chamber 10 and connecting channel 15 act as a diving tube intended to completely empty the product contained in recipient 2, i.e. in second chamber 20. The recipient 2 can clearly be brought into contact with the air in order to compensate for the volume of dispensed product, but it is also possible to create this second chamber without an air intake, for example using a soft bag.

What is claimed is:

1. A device for dispensing fluid products, comprising a dispensing component (1), such as a pump, mounted on a recipient (2), and an actuating component (3), such as a push-button, for dispensing products, the device comprising two product chambers (10, 20) fitted such that they are emptied successively, the product that is contained in the second chamber (20) only being dispensed once the first chamber (10) is empty, characterized in that the first chamber (10) is fastened to the body of the dispensing component (1) or to a support part (9) of said body, said first chamber extending to the bottom of the recipient at least partly inside the second chamber (20); and wherein the first chamber (10) is connected to the dispensing component (1) and the second chamber (20) is connected to said first chamber (10) by a sealing part (30) that prevents the product contained in second chamber (20) from flowing towards the dispensing component (1) for as long as the first chamber (10) contains product and that releases said flow when said first chamber (10) is empty, such that when the device is subsequently actuated the product contained in second chamber (20) is dispensed.

2. The device according to claim 1, wherein said first chamber (10) is constituted in a single part with the dispensing component (1) body or with the support part (9) of said body (1).

3. The device according to claim 1, wherein the first chamber (10) is connected to the dispensing component (1) on one side and comprises a connecting channel (15) with the second chamber (20) on the other side, said first chamber (10) comprising a follow-through piston (30) that is displaced while remaining leaktight in said first chamber (10) each time the device is actuated in order to compensate for a volume of product that is dispensed each time the device is actuated, the displacement of said follow-through piston (30) simultaneously drawing in product from the second chamber (20) in the upstream section of first chamber (10) located behind said follow-through piston (30) in the direction of flow of the product, and when said follow-through piston (30) reaches an end position in which the first chamber (10) is empty, said follow-through piston operates in conjunction with passage means (35) to create a passage between said upstream section of the first chamber (10) and the dispensing component (1), thereby enabling the product drawn in said upstream section of the first chamber (10) and/or remaining in the second chamber (20) to be dispensed.

4. The device according to claim 3 wherein said passage means (35) are constituted by one or more grooves provided at the downstream end of lateral surface (11) of the first chamber (10).

5. A device for dispensing fluid products, comprising a dispensing component (1), such as a pump, mounted on a recipient (2), and an actuating component (3), such as a push-button, for dispensing products, the device comprising two product chambers (10, 20) fitted such that they are emptied successively, the product that is contained in the second chamber (20) only being dispensed once the first chamber (10) is empty, characterized in that the first chamber (10) is fastened to the body of the dispensing component (1) or to a support part (9) of said body, said first chamber extending to the bottom of the recipient at least partly inside the second chamber (20): and wherein the first chamber (10) is connected to the dispensing component (1) on one side and comprises a connecting channel (15) with the second chamber (20) on the other side, wherein the sealing part (30) is a follow-through piston that is displaced while remaining leaktight in said first chamber (10) each time the device is actuated in order to compensate for a volume of product that is dispensed each time the device is actuated, the displacement of said follow-through piston (30) simultaneously drawing in product from the second chamber (20) in the upstream section of first chamber (10) located behind said follow-through piston (30) in the direction of flow of the product, and when said follow-through piston (30) reaches an end position in which the first chamber (10) is empty, said follow-through piston operates in conjunction with passage means (35) to create a passage between said upstream section of the first chamber (10) and the dispensing component (1), thereby enabling the product drawn in said upstream section of the first chamber (10) and/or remaining in the second chamber (20) to be dispensed.

6. The device according to claim 5, wherein said passage means (35) are constituted by one or more grooves provided at the downstream end of lateral surface (11) of the first chamber (10).

* * * * *